United States Patent
Yasuzawa et al.

(10) Patent No.: US 9,952,239 B2
(45) Date of Patent: Apr. 24, 2018

(54) SAMPLE INSPECTION AUTOMATION SYSTEM AND SAMPLE TRANSFER METHOD

(71) Applicant: Hitachi High-Technologies Corporation, Tokyo (JP)

(72) Inventors: Kenichi Yasuzawa, Tokyo (JP); Kenichi Takahashi, Tokyo (JP); Koji Kamoshida, Tokyo (JP); Masashi Akutsu, Tokyo (JP); Shigeru Yano, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 188 days.

(21) Appl. No.: 14/422,717

(22) PCT Filed: Jul. 29, 2013

(86) PCT No.: PCT/JP2013/070408
§ 371 (c)(1),
(2) Date: Feb. 20, 2015

(87) PCT Pub. No.: WO2014/034342
PCT Pub. Date: Mar. 6, 2014

(65) Prior Publication Data
US 2015/0192598 A1 Jul. 9, 2015

(30) Foreign Application Priority Data
Sep. 3, 2012 (JP) ................ 2012-192745

(51) Int. Cl.
*G01N 35/00* (2006.01)
*G01N 35/10* (2006.01)
*G01N 35/04* (2006.01)

(52) U.S. Cl.
CPC . *G01N 35/00603* (2013.01); *G01N 35/00871* (2013.01); *G01N 35/1081* (2013.01);
(Continued)

(58) Field of Classification Search
CPC ............ Y10T 436/11; G01N 35/00603; G01N 35/00594; G01N 35/00584; G01N 35/10
USPC .................. 422/67, 63, 50; 436/43
See application file for complete search history.

(56) References Cited

U.S. PATENT DOCUMENTS

| | | |
|---|---|---|
| 6,255,614 B1 | 7/2001 | Yamakawa et al. |
| 2004/0037680 A1 | 2/2004 | Sato et al. |
| 2006/0018791 A1 | 1/2006 | Riling et al. |
| 2009/0003981 A1 | 1/2009 | Miller |

(Continued)

FOREIGN PATENT DOCUMENTS

| | | |
|---|---|---|
| EP | 2 075 583 A2 | 7/2009 |
| EP | 2 148 204 A1 | 1/2010 |

(Continued)

OTHER PUBLICATIONS

Extended European Search Report received in corresponding European Application No. 13833815.7 dated Mar. 30, 2016.

(Continued)

*Primary Examiner* — Christine T Mui
(74) *Attorney, Agent, or Firm* — Mattingly & Malur, PC (57) ABSTRACT

The invention provides a sample inspection automation system capable of easily, reliably, and efficiently responding to requests for reinspection or addition of inspection items. The sample inspection automation system includes a storage unit having a sample replacing mechanism for transferring a sample from a tray to a sample transfer line. When the system receives sample retrieval information through the communication between an operating unit and a laboratory information system (LIS), or a host system of the sample inspection automation system, the sample is transferred to the appropriate sample treatment unit through the transfer line. Thus, when a request for reinspection or an addition inspection is issued, the sample inspection automation system can efficiently respond to it.

19 Claims, 8 Drawing Sheets

(52) U.S. Cl.
CPC .............. *G01N 2035/00435* (2013.01); *G01N 2035/0425* (2013.01); *G01N 2035/0462* (2013.01); *Y10T 436/11* (2015.01)

(56) References Cited

U.S. PATENT DOCUMENTS

| | | | |
|---|---|---|---|
| 2009/0035867 A1* | 2/2009 | Yagi | ................... G01N 35/1002 436/50 |
| 2013/0061693 A1 | 3/2013 | Sasaki et al. | |

FOREIGN PATENT DOCUMENTS

| | | |
|---|---|---|
| EP | 2 339 353 A1 | 6/2011 |
| JP | 06-074958 | 3/1994 |
| JP | 09-211005 | 8/1997 |
| JP | 2002-022748 | 1/2002 |
| JP | 2009-222535 A | 10/2009 |
| WO | 02/075323 | 9/2002 |
| WO | 2011/148897 | 12/2011 |

OTHER PUBLICATIONS

International Search Report in PCT/JP2013/070408.
Translation of Japanese Office Action received in corresponding Japanese Application No. 2012-192745 dated Mar. 4, 2017.
Japanese Office Action received in corresponding Japanese Application No. 2012-192745 dated Mar. 14, 2017.
Communication Pursuant to Article 94(3) EPC received in corresponding European Application No. 13 833 815.7 dated Oct. 5, 2017.

* cited by examiner

STORAGE-UNIT MONITORING WINDOW — 60

SAMPLE ID [1234567]   NAME OF PATIENT [HIGHTECH HITACHI]

| SAMPLE | MODULE | TRAY POSITION | TRAY # | POSITION | STATUS |
|---|---|---|---|---|---|
| PARENT SAMPLE | AOB-1 | 1 | 0115 | 32 | REANALYSIS |
| AUTOMATIC ANALYZER 1 | SOB-1 | 1 | 4126 | 6 | |
| AUTOMATIC ANALYZER 2 | SOB-2 | 1 | 0203 | 3 | ADDITIONAL ANALYSIS |
| AUTOMATIC ANALYZER 3 | SOB-2 | 5 | 0205 | 5 | |
| STORAGE SAMPLE | AOB-1 | 10 | 0911 | 6 | |

— 61

[RELOAD] — 62   [CLOSE] — 63

FIG. 6

SAMPLE MONITORING WINDOW — 70

| STATUS | CARRIER | SAMPLE ID | PATIENT NAME | RELOAD |
|---|---|---|---|---|
| LOADED | 00024-1 | 1234567 | HIGHTECH HITACHI | |
| LOADED | 00025-3 | 0000001 | NAKA HITACHI | REANALYSIS |
| DISPENSING ERROR | 00026-4 | 0000002 | TARO HITACHI | |
| COMPLETED | 00027-1 | 0000003 | HANAKO HITACHI | |
| COMPLETED | 00031-1 | 9999999 | ICHIRO | |

— 71

RELOAD
⋮
STORAGE UNIT
⋮

— 72

[CLOSE]

| NO | GROUP | COMMENT |
|---|---|---|
| 1 | BIOCHEMICAL/PARENT | |
| 2 | BIOCHEMICAL/DAUGHTER | |
| 3 | URINE | |
| ⋮ | ⋮ | |
| 21 | STORAGE SAMPLE | |
| ⋮ | ⋮ | |

GROUP SETTING WINDOW — 92

[REGISTER] [CLOSE]

FIG. 10

SAMPLE INSPECTION AUTOMATION SYSTEM AND SAMPLE TRANSFER METHOD

TECHNICAL FIELD

The present invention relates a sample inspection automation system that handles samples such as blood, urine, and the like in clinical assay.

BACKGROUND ART

When automatic analyzers are used to analyze samples such as blood, urine, and the like in clinical assay, many treatments need to be performed depending on requests. Examples include centrifugal separation of samples, dispensation of samples into the special vessels of each automatic analyzer, and attachment of barcode labels to sample vessels. Sample inspection automation systems are designed to perform such treatments automatically and are being used in many hospitals and inspections centers for labor saving and higher efficiency.

Vessels containing blood, urine, or other sample are placed on a carrier used to transfer samples (usually called a rack or a sample vessel holder) and loaded into a sample inspection automation system. Depending on what properties are measured, they are subjected to various treatments. Examples include centrifugal treatment, de-capping for removing the caps of the vessels, dispensation of a sample into several vessels (i.e., dispensation to create daughter samples from a parent sample), attachment of barcode labels to daughter sample vessels, capping for attaching caps to the daughter sample vessels, classified storage of parent and daughter samples for later use, and analysis of daughter samples by transferring daughter sample racks to automatic analyzers. Devices that perform such treatments are connected by transfer lines and constitute a sample inspection automation system.

Patent Document 1 discloses a sample inspection automation system in which a common tray is used both in the sample loading unit and in the storage unit and a single holder is used to transfer a sample along the transfer line.

PRIOR ART DOCUMENTS

Patent Documents
 Patent Document 1: International Publication No. WO 2011/148897

SUMMARY OF THE INVENTION

Problem to be Solved by the Invention

Patent Document 1 teaches the method of transferring a sample from the loading unit to the transfer line upon request of reinspection or additional inspection. Although the system of Patent Document 1 ensures the finding of the sample to which a request for reinspection or additional inspection has been issued, the sample needs to be reloaded by moving the tray from the storage unit to the loading unit and manually placing the sample on the tray. This leaves room for automation, and the system is insufficient in terms of labor saving and efficiency.

On the other hand, some automatic analyzers have the function of automatically performing reinspection based on the results of a first-time analysis. Such analyzers occasionally include a buffer mechanism in which a sample is temporarily put on standby for reinspection. However, if it is determined that reinspection is not necessary for the sample, it is transferred out of the buffer mechanism and stored in a storage unit. Because it usually takes time for the doctor to judge the necessity of reinspection or additional inspection of a sample by comprehensively considering the results of all the analyses conducted, the previous measurement values, the medial condition of the patient, and so on, samples are often stored in the storage unit. Thus, when reinspection or additional inspection is requested for a sample, the laboratory technician needs to find the sample among the large number of samples stored in the storage unit and reload it into the loading unit. This places a large burden on the laboratory technician and is also an obstacle to the actualization of speedy analysis.

The present invention has been made in view of the above, and an object of the invention is thus to provide a sample inspection automation system and sample transfer method capable of the easy, reliable, and efficient transfer of samples when reinspection or additional inspection is requested.

Means for Solving the Problem

To achieve the above object, the present invention provides the following system.

A sample inspection automation system comprising: at least one treatment means for performing treatment on samples; at least one analyzing means for analyzing samples on which treatment has been performed; storage means including a refrigerator for storing samples that have been analyzed and storage samples in a cold environment; transfer means for transferring samples; and a host apparatus that instructs the retrieval of a sample from the storage means when a request for an additional analysis is issued for the sample stored in the storage means, wherein the storage means includes a sample replacing mechanism for retrieving any of the samples stored in the refrigerator, and wherein the transfer means transfers the sample retrieved by the sample replacing mechanism to the appropriate one of the treatment means.

The above system can perform various sample treatments if its treatment means is allowed to have various treatment devices depending on the operational needs of the laboratory in which the system is used. Although this specification does not specifically describe what device the treatment means should include, the use of any treatment devices does not affect the scope of the invention.

Effect of the Invention

In accordance with the invention, it is possible to provide a sample inspection automation system and sample transfer method capable of the easy, reliable, and efficient transfer of samples when reinspection or additional inspection is requested.

MODES FOR CARRYING OUT THE INVENTION

An embodiment of the present invention will now be described with reference to the accompanying drawings.

Figure 1:
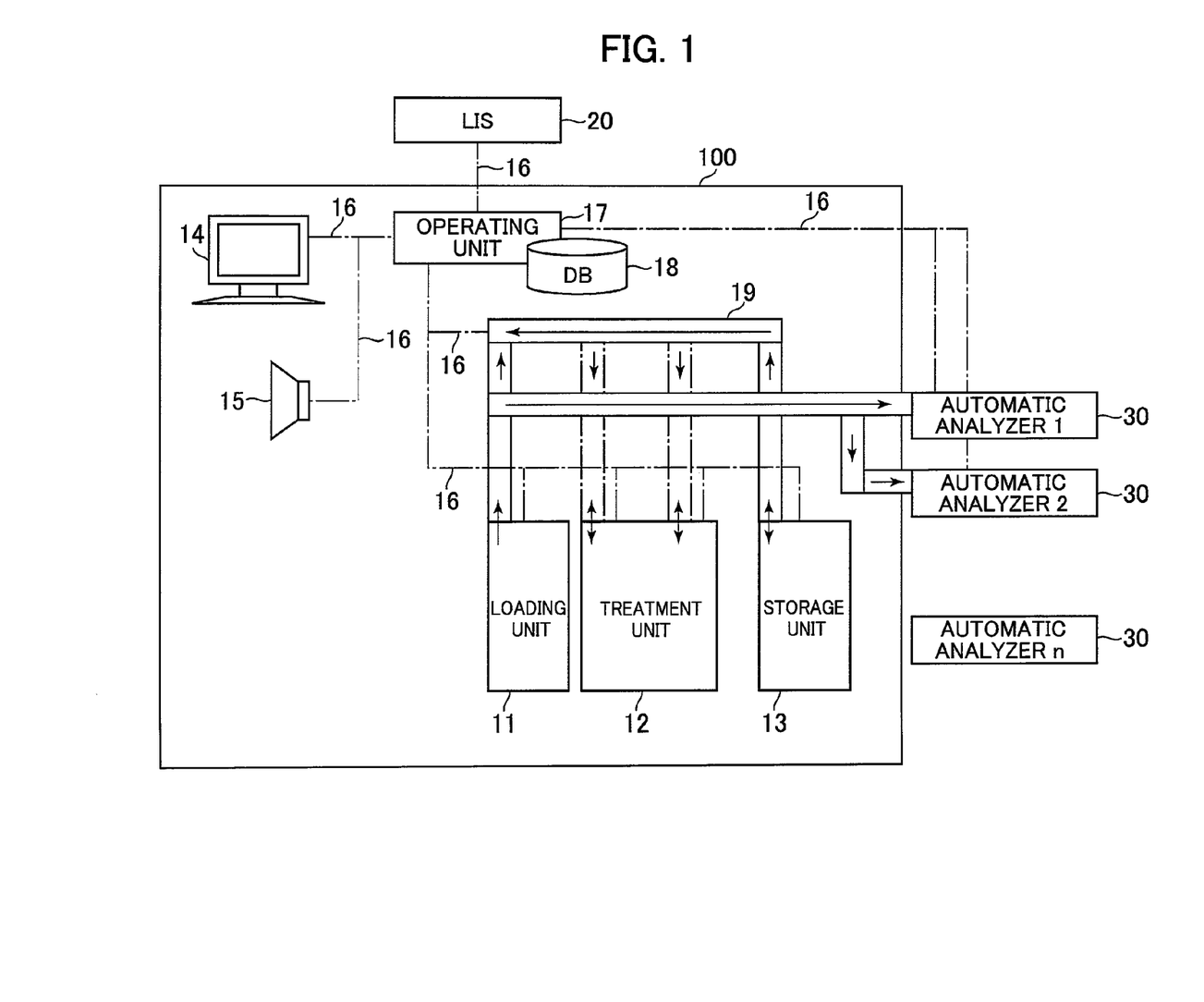
FIG. 1 is a block diagram illustrating the structure of a sample inspection automation system.

FIG. 1 is a block diagram illustrating a system that adopts a sample inspection automation system according to an embodiment of the invention.

The system of FIG. 1 includes automatic analyzers 30 that automatically analyze samples and a sample inspection automation system 100 that optimally performs treatments on samples according to analysis requests and sends them to the automatic analyzers 30.

The sample inspection automation system 100 includes the following components: a sample loading unit 11; a sample treatment unit 12 (not illustrated in detail); a sample storage unit 13; an operating unit 17 having a monitor 14, a speaker 15, and an inter-device communication tool 16; and a transfer line 19 used to transfer a sample from the loading unit 11 to the treatment unit 12, to the storage unit 13, and to the automatic analyzers 30 and transfer the sample from the storage unit 13 back to the loading unit 11 or to the treatment unit 12.

There are two types of the automatic analyzers 30: those assigned numbers, such as the 'automatic analyzer 1' and 'automatic analyzer 2' in FIG. 1, and the one assigned the letter 'n' (i.e., the automatic analyzer n in FIG. 1). Samples are automatically transferred to the former type from the sample inspection automation system 100 through the transfer line 19. On the other hand, the later type needs to be supplied with samples manually by the operator (laboratory technician) because it is not connected to the sample inspection automation system 100.

The operating unit 17 is used to receive request attribute information from an LIS 20 to update a sample information database 18 (DB). The LIS 20 is the acronym of laboratory information system, which is a host system of the sample inspection automation system 100 and controls the entire operation of the system of the invention. The DB 18 stores information regarding the operation of the sample inspection automation system 100 and the automatic analyzers 30; specifically, it stores request attribute information regarding requested analyses on a sample-by-sample basis (i.e., information regarding treatments to be performed by the treatment unit 12 and sample properties to be analyzed by the automatic analyzers 30). The operating unit 17 also controls the sample inspection automation system 100 and the automatic analyzers 30 through the communication tool 16. When an alarm or the like occurs at the sample inspection automation system 100 or any of the automatic analyzers 30, the operating unit 17 displays an alarm notice on the monitor 14 and causes the speaker 15 to output sound so that the laboratory technician can notice it. The operating unit 17 further checks the status of each of the automatic analyzers 30 through the communication tool 16 to examine whether it is available for performing sample analyses.

The loading unit 11 is a module into which the laboratory technician loads a tray having samples thereon; it corresponds to the entrance to the sample inspection automation system 100. Although not illustrated, the loading unit 11 includes at least one mechanism for transferring the samples from the tray to the transfer line 19. Such a mechanism can include, for instance, a chucking mechanism for transferring a sample on the tray to a rack or a holder on the transfer line 19.

Once a sample is transferred to the transfer line 19, its ID is read by an ID reader not illustrated (e.g., a barcode reader or an RFID reader), and the read ID is transmitted to the operating unit 17. The operating unit 17 then examines the DB 18 to see if request attribute information has already been received for the sample or not. Thereafter, the operating unit 17 transmits to the LIS 20 (host system) receipt or non-receipt information indicative of the receipt or non-receipt of request attribute information.

When a request has not been made at the operating unit 17, the LIS 20 transmits the request attribute information of the sample to the operating unit 17. After receiving treatment items to be treated by the treatment unit 12 or inspection items to be analyzed by the automatic analyzers 30 from the request attribute information, the operating unit 17 instructs the loading unit 11 to transfer the sample to the transfer line 19 and to move it to the treatment unit 12 for appropriate treatments.

The storage unit 13 is a module for storing samples after treatment and analysis have been performed on them. The samples are placed on trays in the storage unit 13. The storage unit 13 corresponds to the exit of the sample inspection automation system 100. Although not illustrated, the storage unit 13 includes at least one mechanism for transferring samples from the transfer line 16 to the trays and vice versa, that is, for transferring samples bidirectionally. Similar to the loading unit 11, such a mechanism can include a chucking mechanism for picking up a sample on a rack or a holder to transfer it to a tray of the storage unit 13.

When a sample is to be analyzed by those automatic analyzers 30 that are not connected to the sample inspection automation system 100 via the transfer line 19 such as the automatic analyzer n, the sample is stored in the storage unit 13 after the treatment unit 12 has performed all treatments on it. The operator manually loads the sample stored in the storage unit 13 into the automatic analyzer n to start analysis.

When a sample is to be analyzed by those automatic analyzers 30 that are connected to the sample inspection automation system 100 via the transfer line 19 such as the automatic analyzers 1 and 2, the sample is automatically transferred to the automatic analyzer suitable for the analysis requested after all treatments have been performed on it at the sample inspection automation system 100. After that automatic analyzer has performed all analyses and reinspections on the sample, it is transferred back to the sample inspection automation system 100 via the transfer line 16 and stored in the storage unit 13.

When the LIS 20 transmits request attribute information to the operating unit 17 requesting the reinspection or additional inspection of a sample stored in the storage unit 13, the operating unit 17 instructs the storage unit 13 to transfer the sample to the transfer line 19. Such a sample retrieval instruction can instead be issued from the monitor 14 of the operating unit 17.

Although not illustrated in detail, the treatment unit 12 of FIG. 1 includes various treatment devices to cater the operational needs of the laboratory. Examples of such devices include: a centrifugal treatment module for performing centrifugal treatment on samples in test tubes; a decapping module for removing the caps of the test tubes; a dispensing module for creating daughter samples according to analysis items requested; a barcode labeling module for attaching barcode labels to the vessels of daughter samples created; and a capping module for capping vessels for which all treatments have been performed. Depending on particular treatments to be performed, the treatment unit 12 can include any type or any number of such devices. It should be noted that FIG. 1 is only meant to be an exemplary embodiment, and the order of arrangement of the loading unit 11, the treatment unit 12, and storage unit 13 is not limited to the order shown. In addition, those components need not be arranged in a straight line.

Figure 2:
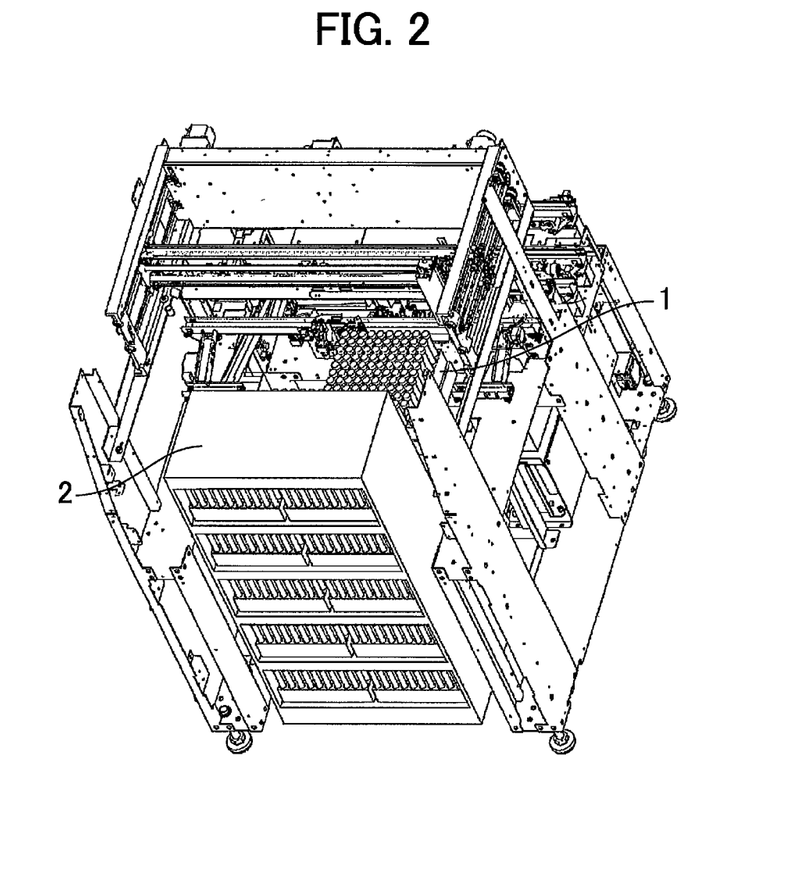
FIG. 2 illustrates the internal structure of a storage unit.

FIG. 2 is a diagram illustrating the internal structure of a storage module constituting the storage unit 13.

The storage module includes two side lifters 1 that are driven independently and a refrigerator 2 that stores multiple trays vertically. When a sample arrives at the storage module to be stored, a sample chucking mechanism (not illustrated) is used to grab the sample and place it on a tray supported by the lifters 1. Each tray includes multiple holding units for holding samples. When all the holding units of a tray are filled with samples, the tray is transferred from the lifters 1 to the refrigerator 2 to be stored in a cold dark environment. Thus, after treatments and analyses have been performed on samples, they can be stored without deterioration.

Although not illustrated in FIG. 2, the lifters 1 are capable of moving vertically to access each stage of the refrigerator. When a tray is transferred from the lifters 1 to the refrigerator 2, the tray is slide from the lifters 1 to the refrigerator 2, whereby the tray can be moved smoothly between the lifters 1 and the refrigerator 2.

Some of the automatic analyzers 30 are designed to automatically perform reinspection based on the results of a first-time analysis. Such automatic analyzers occasionally include a buffer mechanism for temporarily storing samples for later reinspections. Because the necessity of a reinspection is judged on the basis of the results of the first-time analysis, the judgment can be made in a short amount of time in most cases.

On the other hand, when it is determined that a sample does not need a reinspection, it is transferred to the storage unit for storage, based on the assumption that analyses are complete for the sample. In a conventional apparatus, once the sample is stored in the storage unit, the laboratory technician needs to search the storage unit for the sample and bring it back to the loading unit 11 if the doctor determines that a reinspection or the addition of inspection items is necessary for the sample by comprehensively considering the results of all the analyses conducted, the previous values, the medial condition of the patient, and so on.

The storage unit 13 of the invention is optimal in that it allows reinspections or additional inspections to be conducted automatically after the passage of a certain amount of time since samples were stored in the storage unit. Thus, the storage unit 13 is capable of storing samples until the end of the day when analyses were performed on them, or more preferably for several days until they are disposed of.

Figure 3:
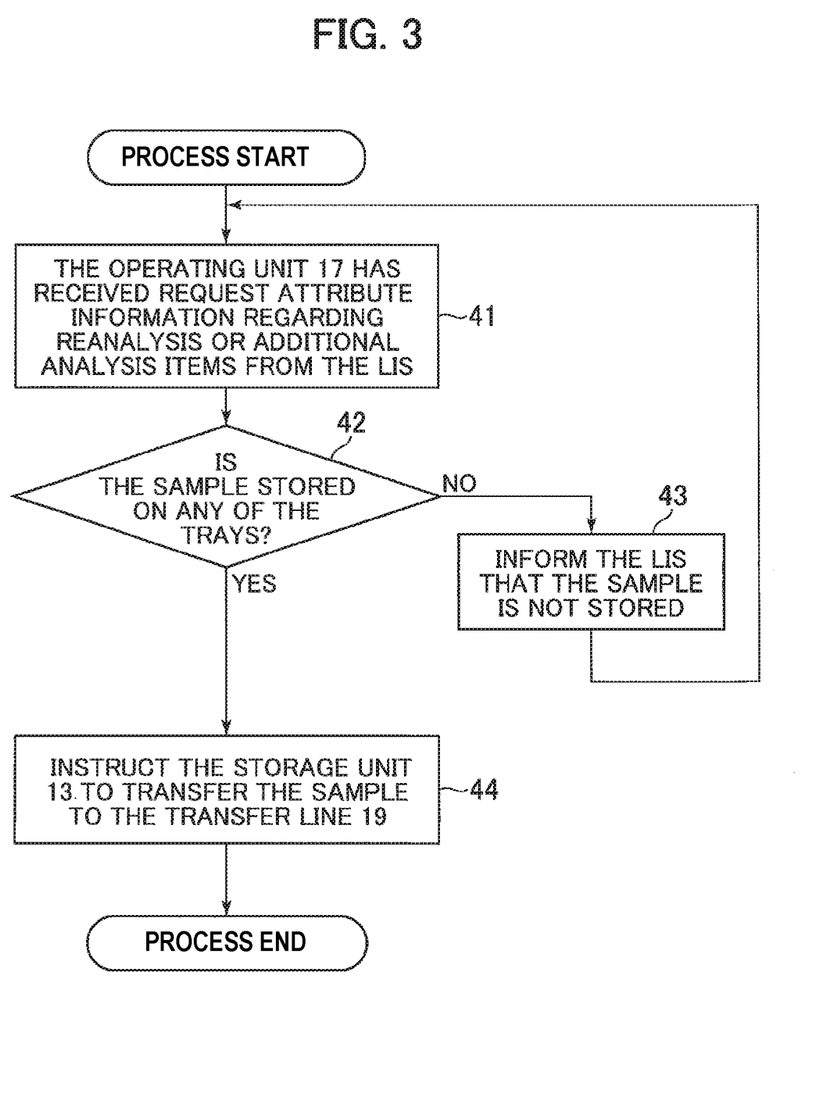
FIG. 3 is a flowchart illustrating an example of the process performed upon receipt of request attribute information regarding reinspection or additional inspection items from an LIS.

FIG. 3 is a flowchart illustrating an example of the process performed by the operating unit when it receives request attribute information regarding reinspection or additional inspection items from the LIS 20.

When it is determined that reinspection or additional inspection is necessary and the operating unit 17 receives request attribute information regarding items from the LIS 20 (Step 41), the operating unit 17 searches the DB 18 to see if the sample is stored in a tray of the storage unit 13 (Step 42). If not, the operating unit 17 informs the LIS 20 that the sample is not in the storage unit 13 and waits again for information from the LIS 20 (Step 43). If the sample is stored in a tray of the storage unit 13, operating unit 17 instructs the storage unit 13 to transfer the sample to the transfer line 19 (Step 44). Although not illustrated, when a request for reinspection or addition of inspection items is made for a sample and it is not stored in a tray of the storage unit 13, alarm information is displayed on the monitor 14 of the operating unit 17 with the speaker 15 outputting sound.

Instead, the display of the alarm information and the sound output can be effected only after the operating unit 17 transmits information indicative of the non-presence of the sample to the LIS 20 a particular number of times. In that case, the display unit 14 is configured to display a parameter screen with which the operator sets that particular number.

The status of each automatic analyzer 30 can be known through the communication tool 16. Thus, when the LIS 20 issued a request for reinspection or addition of inspection items for a sample and the automatic analyzer 30 that is supposed to analyze the sample is not capable of performing analysis due to failure or the like, it is also possible to inform the laboratory technician of the fact by the display of alarm information and by the output of sound, as is similar to the case where such a sample is not stored in the storage unit 13.

Figure 4:
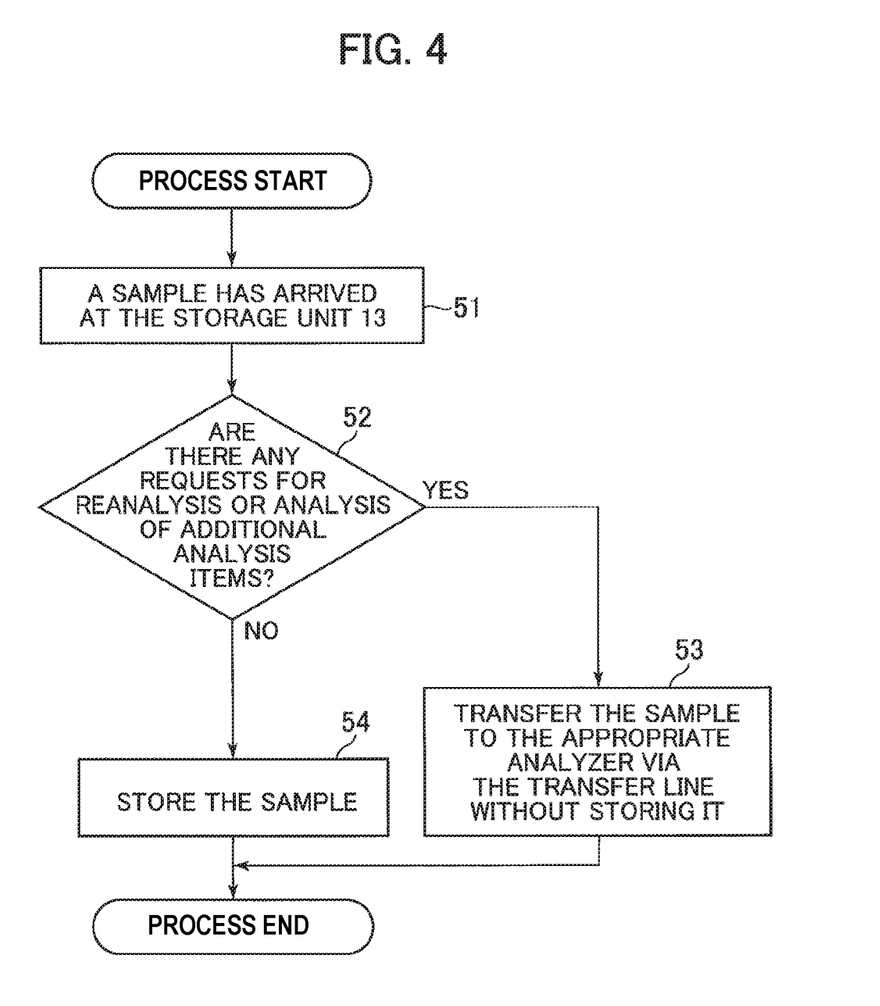
FIG. 4 is a flowchart illustrating an example of the process performed when a sample arrives at a storage unit.

FIG. 4 is a flowchart illustrating an example of the process performed when the LIS 20 issued request attribute information regarding reinspection or addition of inspection items for a sample and the sample has been transferred from another module to the storage unit 13.

When all requested treatments and analyses have been performed on the sample, it is transferred to the storage unit 13 to be stored. After an ID reader recognizes the arrival of the sample at the storage unit 13 (Step 51), it is determined whether the LIS 20 has issued a request for reinspection or addition of inspection items for the sample or not (Step 52). If not, the sample is stored in a tray of the storage unit 13 without further processes (Step 54).

If so, the sample is transferred to the appropriate automatic analyzer 30 via the transfer line 19 without being stored in the storage unit 13 (Step 53). Thus, by allowing the sample to pass through the storage unit 13 without being stored therein when the LIS 20 issued a request for reinspection or addition of inspection items, the unnecessary storage and retrieval of the sample in/from the storage unit 13 can be avoided, resulting in speedy inspections.

Depending on the operational needs of the laboratory, it is necessary to transfer a parent sample (i.e., original sample) to an automatic analyzer 30 for analysis, as well as daughter samples created by dispensing part of the parent sample. Depending on inspection items requested, the parent sample may also need to be transferred to several analyzers 30. In such a case, the parent sample will not be transferred back to the storage unit 13 until all the analyzers 30 perform necessary analyses, and the operating unit 17 may receive from the LIS 20 a sample retrieval instruction together with a request for reinspection or addition of inspection items. Thus, sample retrieval information associated with requests for reinspection or addition of inspection items is stored on the DB, which manages the information of all samples handled by the system, so that the positions of samples along the transfer line 19 can be known. This prevents samples from being stored in the storage unit 13 when they arrive at the storage unit 13 and storage of the samples is determined to be unnecessary.

In addition, reinspections or additional inspections requested by the doctor are often given a higher priority than normal first-time inspections. Thus, it is effective to transfer samples to the treatment unit 12 and to automatic analyzers 30 as soon as possible by skipping the unnecessary storage and retrieval of the samples.

Although not illustrated in FIG. 4, if the timing of receiving from the LIS 20 request attribute information regarding reinspection or addition of inspection items for a sample occurs during the time period between the storage of the sample in a tray of the storage unit 13 and the arrival of a next sample at the storage unit 13, the former sample can be transferred from the tray to the transfer line 19 immediately. Thus allows the requested reinspection or additional inspection to be performed preferentially on the former sample.

Figure 5:
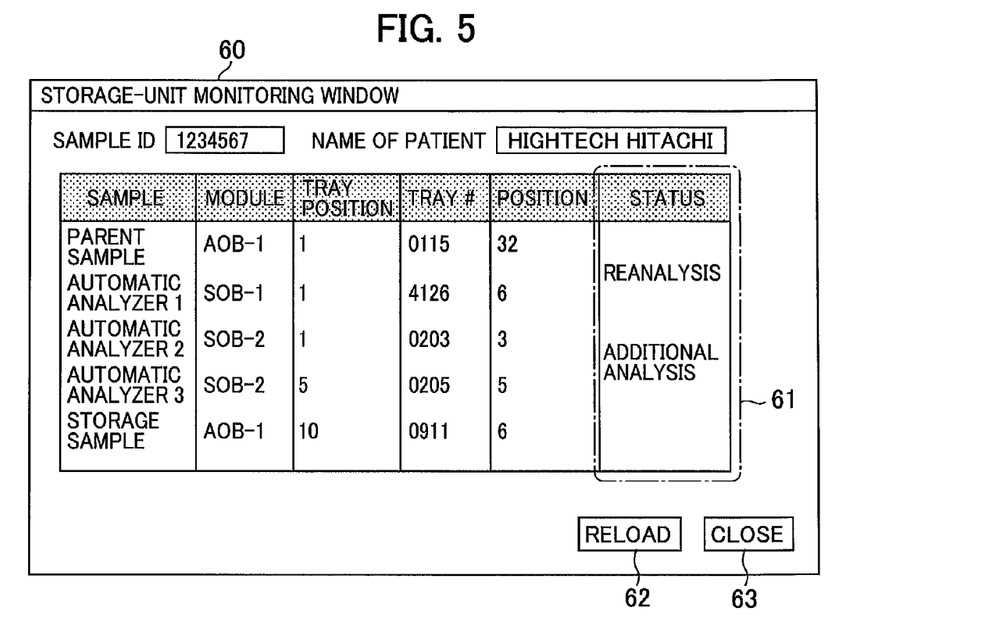
FIG. 5 illustrates a storage-unit monitoring window.

FIG. 5 illustrates a storage-unit monitoring window 60 displayed on the monitor 14 of the operating unit 17 with which to instruct the retrieval of samples from the storage unit 13.

As already stated, it is the LIS 20 that issues sample retrieval instructions to perform reinspection or inspection of additional items. However, the use of the storage-unit monitoring window 60 also allows the laboratory technician to issue such sample retrieval instructions.

Inside the storage-unit monitoring window 60 are the name of a sample (or sample ID; for instance, '1234567' as displayed on the sample ID box), the modules in which samples are currently located, the tray numbers of the modules, the positions on the trays, and the status of the samples. The status of the samples is displayed in a status box 61. Specifically, the status box 61 shows the necessity of reinspection or additional inspection of the samples. The laboratory technician can view the status box 61 to determine which samples need to be retrieved from the storage unit 13. If it is determined that a particular sample needs to be retrieved from the storage unit 13 and reloaded, he or she can select the sample and press (or click on) a reload button 62, whereby sample retrieval information is transmitted to the storage unit 13.

Although not illustrated in FIG. 5, the reload button 62 can be shown active only when a request for reinspection or additional inspection has been issued for a selected sample. This allows the laboratory technician to see clearly if there are such requests and prevents operational errors.

Further, depending on the operational needs of the laboratory, a reinspection or an additional inspection of a sample may require the reloading of its parent sample or the reloading of storage samples that are created by extracting almost all the serum components from the parent sample and stored in reparation for reinspection or addition of inspection items. Thus, a parameter window on the monitor 14 (not illustrated) can be used to determine which of the two, the parent sample or the storage samples, is loaded at the time of reloading. This is suitable when only either of the two is consistently loaded. Alternatively, two reload buttons 62 can be provided, and one is used to reload the parent sample and the other to reload the storage samples. This method is suitable when the laboratory technician switches between the parent sample and the storage samples during the operation of the system. Thus, in the latter case, the names of the two reload buttons 62 on the screen should be differentiated.

Figure 6:
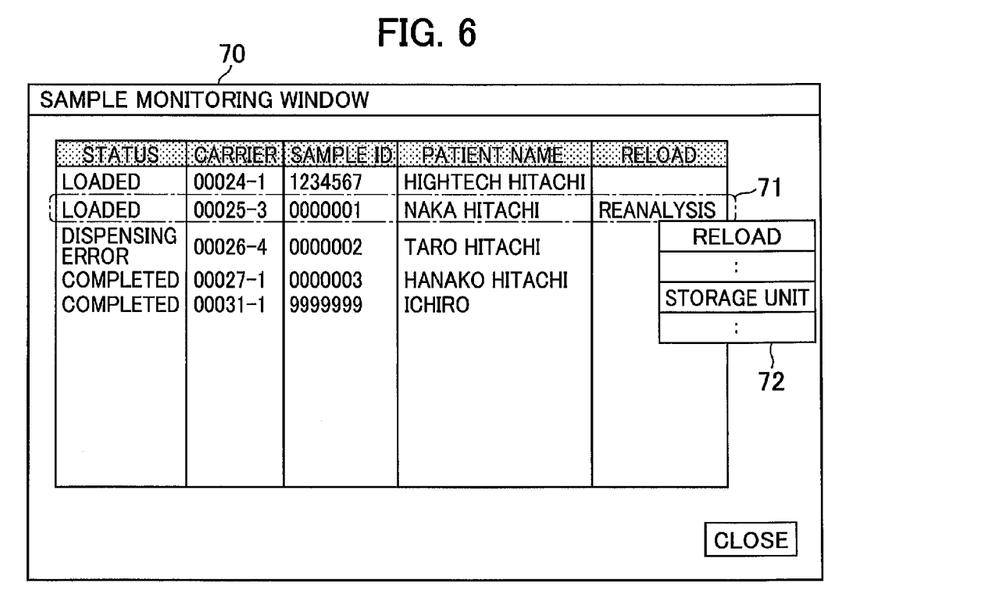
FIG. 6 illustrates a sample monitoring window.

FIG. 6 illustrates a sample monitoring window 70 that lists the samples handled by the sample inspection automation system 100 and used to issue a reload instruction upon request of reinspection or addition inspection.

The table of the sample monitoring window 70 displays the following for each sample: the status of the sample, the ID of the carrier that transferred the sample, the ID of the sample, the name of the patient, and reloadability. As illustrated in FIG. 6, the information regarding a sample is displayed in a row. By selecting a sample for which reloading is necessary (as indicated by the chain line 71 of FIG. 6) and then pressing the right button of a mouse (not illustrated), a pull-down menu 72 is displayed. The pull-down menu 72 shows instructions to be issued to the sample. When the laboratory technician selects 'Reload' in the pull-down menu 72, sample retrieval information is transmitted to the storage unit 13. The sample monitoring window 70 can instead be configured to accept the simultaneous selection of several samples and an instruction to perform reloading for all the selected samples.

By selecting a sample in the list of the sample monitoring window 70 to display the pull-down menu 72 and then selecting 'Storage Unit' in the menu 72, the storage-unit monitoring window 60 can be displayed. When the 'Close' button 63 in the storage-unit monitoring window 60 is pressed, the sample monitoring window 70 will reappear. In this manner, it is preferred that the two windows 70 and 60 operate in conjunction with each other.

Figure 7:
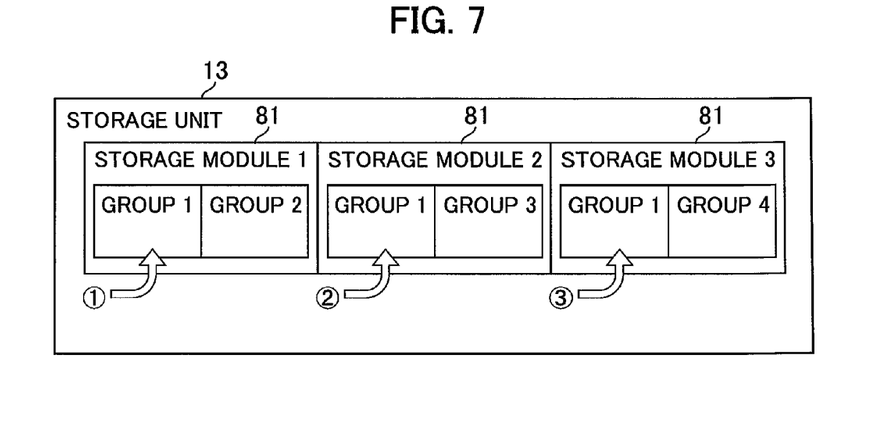
FIG. 7 illustrates an example of how to manage the storage of samples in a storage unit including a plurality of storage modules.

FIG. 7 illustrates an example of how to manage the storage of samples in the storage unit 13 including a plurality of storage modules 81.

In this example, the storage unit 13 is constructed by connecting the plurality of storage modules 81. As illustrated in FIG. 2, each storage module 81 includes two side lifters 1, a multi-stage refrigerator 2, a plurality of trays on which to place samples (the trays can be moved between the lifters 1 and the refrigerator 2), and a sample replacing mechanism such as a chucking mechanism for grabbing a sample to place it on a tray. The storage modules 81 store samples according to the groups classified by the type and attributes of the samples. In the example of FIG. 7, storage modules 1, 2, and 3 store samples of groups 1 and 2, samples of groups 1 and 3, and samples of groups 1 and 4, respectively.

When samples of the same group (such as group 1) are successively stored and the group is shared by the storage modules 81, they are stored alternately to the modules 81 for the purpose of improving efficiency. Transferring a sample to a tray by the chucking mechanism involves multiple steps: grabbing the sample, moving upward, moving horizontally, moving downward, and placing the sample on the tray. Thus, if samples are successively transferred to the same storage module, its sample replacing mechanism cannot transfer the samples fast enough, resulting in a jam in front of the module.

To prevent this, one possible method would be to provide each storage module with multiple sample replacing mechanisms and to use the mechanisms alternately. However, the use of multiple sample replacing mechanisms complicates the structure of the modules and the control method and also increases the cost of the modules. For instance, if multiple chucking mechanisms are used in a storage module, the module needs to have multiple arm mechanisms for holding sample vessels, multiple drive mechanisms for vertically moving the arm mechanisms, and multiple drive mechanisms for driving the arm mechanisms in x- and y-directions. Besides, each of the chucking mechanism needs to be controlled such that the operation of a chucking mechanism does not interfere with the operation of the others.

Therefore, in the present embodiment, when samples of the same group successively arrive at the storage unit 13, they are stored sequentially in the storage module 1, the storage module 2, the storage module 3, the storage module 1, . . . , in the stated order. Thus, when such samples are transferred along the transfer line 19 to be placed on trays, they can be stored smoothly in a separate manner in the storage unit 13 without causing a jam. Such dispersed storage of samples among the storage modules 81 allows, for instance, the sample replacing mechanism of the storage module 2 to store a sample while the sample replacing mechanism of the storage module 1 is storing a sample; thus, the time loss involved in the storage can be reduced.

As stated above, when samples belonging to group 1 successively arrive at the storage unit 13, the storage modules to which group 1 has been allocated are selected (i.e., the storage modules 1, 2, and 3 in the example of FIG. 7), and the samples are stored alternately to those modules. On the other hand, when samples of different groups alternately arrive at the storage unit 13, a sample identifying device determines in advance which group each of the samples belongs to, and the destinations of storage are dispersed so that they are not stored successively in the same module if possible. For example, when it is determined that a sample of group 1 is followed by a sample of group 2, the sample of group 1 is stored in the storage module 2 or 3 so that the sample of group 2 can be stored in the storage module 1 without making it wait.

When, for instance, the storage module 2 among the storage modules 81 is not available for use due to failure or the like, samples of group 1 can be stored alternately in the storage modules 1 and 3; thus, the storage of the samples in the storage module 2 is avoided.

Also, in the above case, samples of group 3 are transferred to an error position without being stored in any of the storage modules because group 3 is also allocated to the storage module 2. In this case, the system needs to be operated by the modules that are available for use (i.e., without the storage module 2). While the storage module 2 is not available, it is effective to temporarily change the parameter settings (described below) to set the storage destination of samples of group 3 to the storage module 1 or the storage module 3.

Figure 8:
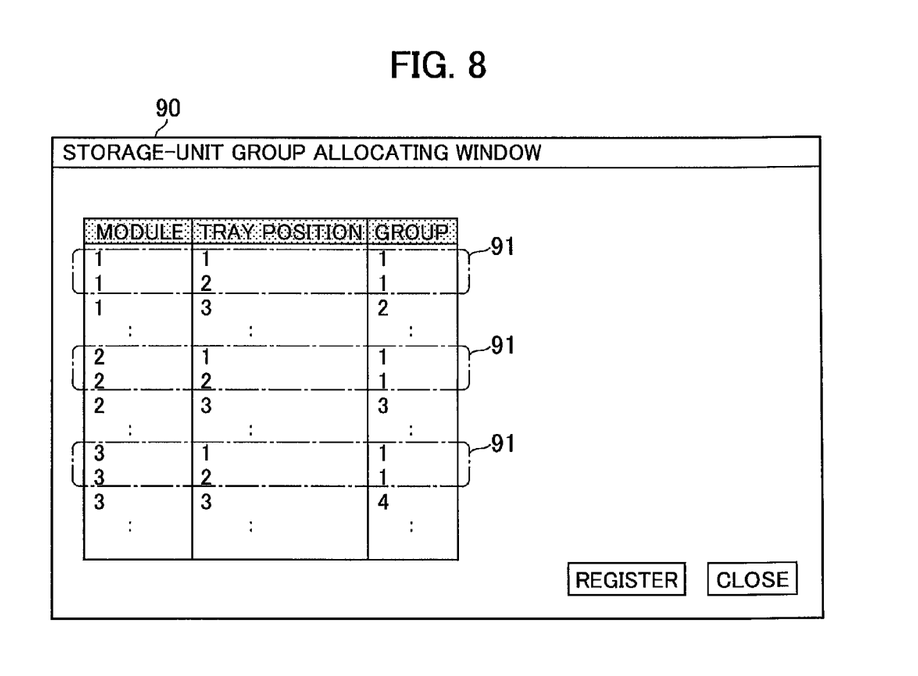
FIG. 8 illustrates a storage-unit group allocating window.

FIG. 8 illustrates a storage-unit group allocating window 90 for allocating sample groups to the modules of the storage unit.

As illustrated in the group allocating window 90, by allocating the same group to multiple trays of each of the storage modules 81 (as in the same-group markings 91), the alternate sample transfer to the storage modules 81 as in FIG. 7 can be achieved. Because the numbers of the modules and the positions of the trays are often fixed, the operator can assign group numbers (1, 2, . . . ) to the trays of the modules. After the input of the group numbers, the operator can click on the 'Register' button to reflect the parameters set on the group allocating window 90.

The group allocating window 90 allows group allocation to be changed even during the operation of the system. For instance, even if one storage module goes out of order as in the previous case, group allocation can be changed right after the event, thereby continuing the operation of the system without interrupting the other storage modules that are in operation. While FIG. 8 shows an example in which groups are allocated on a tray-by-tray basis, multiple groups can instead be allocated to a single tray.

Figure 9:
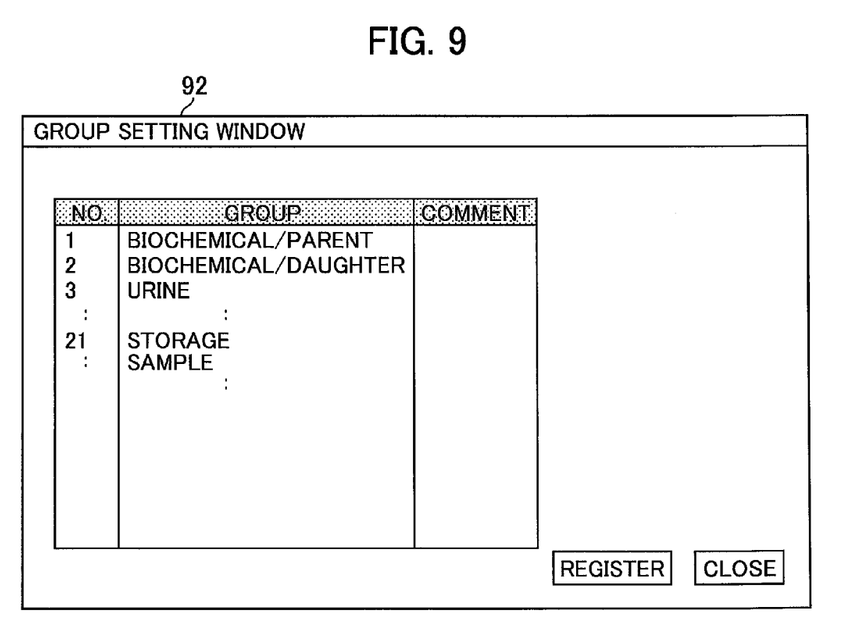
FIG. 9 illustrates a group setting window.

FIG. 9 illustrates a group setting window 92 for determining sample groups according to which samples are stored.

The group setting window 92 is used to determine the numbers of groups to be allocated to the trays of the storage modules using the storage-unit group allocating window 90 and the attributes of samples belonging to the groups. On the group setting window 92, one or more group names can be registered. In the example of FIG. 9, samples of group 1 are parent samples for which the analysis of biochemical items has been requested, and samples of group 2 are daughter samples for which the analysis of biochemical items has been requested. In addition, samples of group 3 are urine samples, and samples of group 21 are storage samples.

The classification of groups can be based on the types of samples (e.g., serum samples, whole blood samples, urine sample, etc.), but sample types for which analysis is requested less frequently (e.g., urine samples, clotted samples, etc.) can be classified into a single group (for instance, into 'Others' group).

As in FIG. 7, the best way to allocate sample groups is to allocate group 1, in which the number of samples is the largest, to all the storage modules 1, 2, and 3 and to allocate groups 2, 3, and 4, for which analysis is requested less frequently, to the storage modules 1, 2, and 3, respectively. This group allocation method is effective in preventing samples from causing a jam on the transfer line 19.

Figure 10:
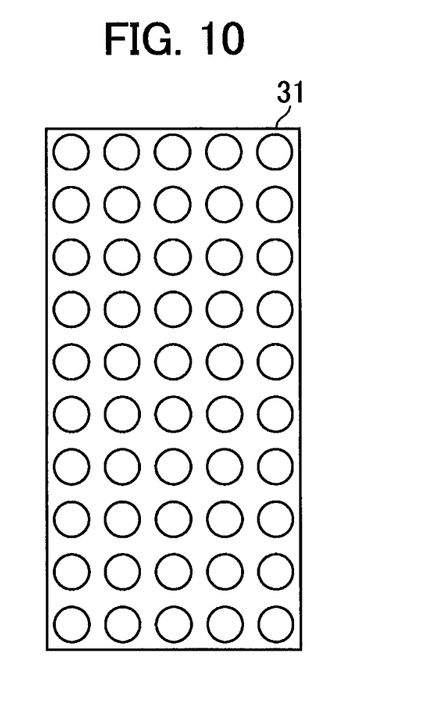
FIG. 10 illustrates a tray on which to place samples.

FIG. 10 illustrates a tray 31 used in the storage unit 13.

The storage unit 13 stores samples and transfers any of the samples from its refrigerator back to the transfer line 19 when instructed to do so. A sample transferred back to the transfer line 19 from the storage unit 13 is ideally restored in the same position on the tray 31 after the completion of the reinspection or additional inspection requested. However, there may be a case where the sample will not return to the storage unit 13 if it was transferred to the error position due to a dispensing error. If that happens frequently, the tray 31 will have multiple vacant positions. When there are many vacant positions on the tray 31, the number of samples the storage unit can store is reduced accordingly, and the number of trays 31 that need to be used increases as well. If all the samples within the storage unit 13 need to be stored in another refrigerator after the end of a day's analysis, the operator needs to transport more trays 31, which is time-consuming.

Thus, it is effective to fill the vacant positions on the tray 31 by rearranging the samples on it after the end of a day's analysis or after data initialization. In that case, the positional information of the samples has to be updated and stored in the operating unit 17. Because wrong positional information results in a false analysis report and an inappropriate medical examination, the ID reader of the storage unit 13 (not illustrated) reads the IDs (barcodes or the like) of the samples again before rearranging them. The filling of the vacant positions on the tray 31 reduces the number of trays 31 to be used and reduces the manual labor by the laboratory technician.

In accordance with the sample inspection automation system of the foregoing embodiment, it is possible to easily, reliably, and efficiently respond to requests for reinspection or addition of inspection items.

DESCRIPTION OF THE REFERENCE NUMERALS

1: Lifter
2: Refrigerator
11: Sample loading unit
12: Sample treatment unit
13: Sample storage unit 14: Monitor
15: Speaker
16: Communication tool
17: Operating unit
18: Database
19: Transfer line
20: LIS
30: Automatic analyzer
31: Tray
60: Storage-unit monitoring window
61: Status box
62: Reload button
63: Close button
70: Sample monitoring window
72: Pull-down menu
81: Storage module
90: Storage-unit group allocating window
91: Same-group marking
92: Group setting window
100: Sample inspection automation system

The invention claimed is:

1. A sample inspection automation system comprising:
at least one treatment means for performing treatment on samples;
at least one analyzing means for analyzing samples on which treatment has been performed;
a storage means including a refrigerator for storing samples in a cold environment that have been analyzed and a sample replacing mechanism for retrieving any of the samples stored in the refrigerator;
a transfer means for transferring samples between the treatment means, storage means and the at least one analyzing means; and
a controller, including a memory, programmed to:
instruct the retrieval of a sample from the storage means when a request for an additional analysis is issued for the sample stored in the storage means that has been previously analyzed by an analyzing means, and
instruct the transfer means to transfer the sample retrieved by the sample replacing mechanism to a treatment means,
wherein the storage means includes a plurality of storage modules,
wherein the controller is further programmed to store in the memory, a group, of a plurality of groups, that each sample belongs to and allocate the plurality of groups of samples to the plurality of storage modules, such that each group is allocated to at least one storage module, and allocate one group of the plurality of groups of samples to at least two of the plurality of storage modules,
wherein samples that are transferred to the storage means are stored in a storage module according to the group the sample belongs to, and
wherein when samples belonging to the one group are transferred successively to the storage means, the samples are successively stored in different storage modules.

2. The sample inspection automation system of claim 1, further comprising:
a communication means connected to the controller for outputting information indicating that a sample for which the controller has issued a retrieval request is not in the storage means.

3. The sample inspection automation system of claim 1, wherein if a sample for which the controller has issued a retrieval request is transferred to the storage means, the transfer means transfers the sample to a treatment means without storing the sample in the storage means.

4. The sample inspection automation system of claim 1, wherein the controller is further programmed to issue requests including sample retrieval requests.

5. The sample inspection automation system of claim 4, wherein the controller is further programmed to specify which samples need be retrieved.

6. The sample inspection automation system of claim 1, wherein the controller is further programmed to determine the samples stored by each storage module.

7. The sample inspection automation system of claim 6, wherein the controller is further programmed to set groups that the samples belong to based on a type of the sample.

8. The sample inspection automation system of claim 1, wherein the storage means has at least one tray that stores samples thereon, and
wherein the samples on the tray are rearranged to fill vacant positions on the tray after detecting a particular event.

9. A sample transfer method for use in a sample inspection automation system, the system comprising:
at least one treatment means for performing treatment on samples;
at least one analyzing means for analyzing samples on which treatment has been performed;
a transfer means for transferring samples between the treatment means, storage means and the at least one analyzing means; and
a storage means including a refrigerator for storing samples in a cold environment that have been analyzed, the storage means including a plurality of storage modules,
the method comprising the steps of:
if a request for an additional analysis is issued for any of the samples stored in the storage means that has been previously analyzed by an analyzing means, retrieving the sample from the storage means and transferring the sample to an appropriate one of the analyzing means capable of analyzing the requested analysis item;
storing a group, of a plurality of groups, that each sample belongs to;
allocating the plurality of groups to different storage modules of the storage means, such that each group is allocated to at least one storage module, allocating one of the groups is allocated to at least two of the plurality of storage modules; and
storing samples that are transferred to the storage means in a storage module according to the group the sample belongs to,
wherein when samples belonging to the one group are transferred successively to the storage means, the samples are successively stored in different storage modules.

10. The sample transfer method of claim 9, further comprising:
outputting information indicating that a sample for which a request for an additional analysis has been issued is not stored in the storage means.

11. The sample transfer method of claim 9, further comprising:
for a sample for which a request for an additional analysis has been issued arrives at the storage means, transferring the sample to the appropriate one of the analyzing means without being stored in the storage means.

12. The sample transfer method of claim 9, further comprising:
   setting groups that the samples belong to based on a type of the sample.

13. The sample transfer method of claim 9,
   wherein each of the plurality of storage modules has at least one tray that stores samples thereon, and
   wherein the samples on the tray are rearranged to fill vacant positions on the tray at a particular timing.

14. The sample inspection automation system of claim 1,
   wherein when samples belonging to different groups are successively transferred to the storage means and a second sample of the successively transferred samples belongs to the one group allocated to the at least two of the storage modules, the second sample successively transferred is stored in a different storage module than a storage module that a first sample of the successively transferred sample is stored.

15. The sample transfer method of claim 9, further comprising:
   wherein when samples belonging to different groups are successively transferred to the storage means and a second sample of the successively transferred samples belongs to the one group allocated to all of the storage modules, storing the second sample successively transferred in a different storage module than a storage module that a first sample of the successively transferred sample is stored.

16. The sample inspection automation system of claim 1,
   when samples belonging to the one group allocated to the at least two of the storage modules are successively transferred to the storage means, each of two successive samples belonging to the one group is stored in a different storage module.

17. The sample transfer method of claim 9, further comprising;
   when samples belonging to the one group allocated to the at least two of the storage modules are successively transferred to the storage means, storing each of two successive samples belonging to the same group in a different storage module.

18. The sample inspection automation system of claim 14,
   wherein the one group is allocated to the storage module that the first sample is stored.

19. The sample transfer method of claim 15, further comprising:
   wherein the one group is allocated to the storage module that the first sample is stored.

* * * * *